US012678125B2

(12) United States Patent
Fujii et al.

(10) Patent No.: US 12,678,125 B2
(45) Date of Patent: Jul. 14, 2026

(54) ULTRASOUND DIAGNOSTIC APPARATUS

(71) Applicant: FUJIFILM Corporation, Tokyo (JP)

(72) Inventors: Nobuhiko Fujii, Tokyo (JP); Katsunori Asafusa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/917,903

(22) Filed: Oct. 16, 2024

(65) Prior Publication Data

US 2025/0127482 A1     Apr. 24, 2025

(30) Foreign Application Priority Data

Oct. 18, 2023     (JP) ................................. 2023-179563

(51) Int. Cl.
| | |
|---|---|
| *A61B 8/06* | (2006.01) |
| *A61B 8/00* | (2006.01) |
| *A61B 8/02* | (2006.01) |
| *G01S 7/52* | (2006.01) |

(52) U.S. Cl.
CPC ................. *A61B 8/06* (2013.01); *A61B 8/02* (2013.01); *A61B 8/488* (2013.01); *G01S 7/52057* (2013.01); *A61B 8/461* (2013.01)

(58) Field of Classification Search
CPC .. A61B 8/06; A61B 8/488; A61B 8/02; G01S 7/52066; G01S 7/52057
See application file for complete search history.

(56) References Cited

U.S. PATENT DOCUMENTS

| | | | |
|---|---|---|---|
| 6,245,018 B1 | 6/2001 | Lee | |
| 2004/0102706 A1* | 5/2004 | Christopher | ........ G01S 7/52026 |
| | | | 600/453 |
| 2018/0203104 A1 | 7/2018 | Fujii | |
| 2020/0405270 A1* | 12/2020 | Ota | ......................... A61B 8/06 |

FOREIGN PATENT DOCUMENTS

| | | |
|---|---|---|
| JP | H11-235342 A | 8/1999 |
| JP | 2005-185731 A | 7/2005 |
| JP | 2010-088943 A | 4/2010 |
| JP | 2016-087302 A | 5/2016 |

OTHER PUBLICATIONS

Extended European Search Report issued in EP 24 20 7282.5—1122 by the European Patent Office on Mar. 4, 2025, which is related to U.S. Appl. No. 18/917,903.
Takashi Itoh, "Ultrasonic Imaging System," Journal of the Electrophotography Society, 1990, pp. 180-187, vol. 29, No. 2.

* cited by examiner

*Primary Examiner* — John D Li
(74) *Attorney, Agent, or Firm* — Studebaker Brackett PLLC

(57)     ABSTRACT
An ultrasound diagnostic apparatus includes a transmission unit, a reception unit, and an information processing unit. The transmission unit transmits an ultrasonic wave to a subject via an ultrasound probe. The reception unit receives the ultrasonic wave reflected by the subject via the ultrasound probe. The information processing unit executes processing on a reception signal output from the reception unit. The information processing unit generates Doppler waveform data based on the reception signal, obtains a maximum value, a minimum value, and a reference value of a Doppler waveform line obtained from the Doppler waveform data, and decides a display range of blood flow velocity indicated by a Doppler waveform based on the maximum value, the minimum value, the reference value.

3 Claims, 11 Drawing Sheets

FIG. 1

ULTRASOUND DIAGNOSTIC APPARATUS

CROSS-REFERENCE TO RELATED APPLICATIONS

This application claims benefit of priority to Japanese Patent Application No. 2023-179563 filed Oct. 18, 2023, the entire contents of which are incorporated herein by reference.

BACKGROUND OF THE INVENTION

1. Field of the Invention

The present disclosure relates to an ultrasound diagnostic apparatus, and particularly relates to processing for displaying a Doppler waveform.

2. Description of the Related Art

An ultrasound diagnostic apparatus that observes a subject by transmitting and receiving ultrasonic waves has been widely used. In general, the ultrasound diagnostic apparatus has a function of displaying a Doppler waveform indicating blood flow velocity. Waveform characteristic values such as a maximum value, a minimum value, and an average value of the Doppler waveform vary depending on an observation site. Therefore, a technique has been developed for adjusting a scale in displaying the Doppler waveform, thereby making it easier for a user to observe the Doppler waveform.

JP2010-88943A discloses that a Doppler velocity range is adjusted based on a statistical value of a distribution of at least one of maximum flow velocity or average flow velocity of a trace waveform of a spectrum signal in a frequency direction. In addition, JP2010-88943A discloses obtaining a baseline and multiples of how many times estimated values of an upper limit and a lower limit of the velocity range are set as a display range, based on a positive side maximum value and a negative side maximum value.

JP1999-235342A (JP-H11-235342A) discloses that, in an ultrasound color Doppler video system, it is determined whether a blood vessel as a diagnosis target is an artery or a vein based on a pulsation index PI and a resistance index RI of blood flow velocity. JP2016-87302A discloses a technique of generating Doppler image data representing blood flow velocity using color.

SUMMARY OF THE INVENTION

The waveform characteristic values of the Doppler waveform varies depending on the observation site. Therefore, in a case in which the Doppler waveform is displayed at a certain scale, it may become difficult to see the Doppler waveform.

An object of the present disclosure is to set a display state of a Doppler waveform so that the Doppler waveform is easily visible.

According to the present disclosure, there is provided an ultrasound diagnostic apparatus comprising: a transmission unit that transmits an ultrasonic wave to a subject via an ultrasound probe; a reception unit that receives the ultrasonic wave reflected by the subject via the ultrasound probe; and an information processing unit that executes processing on a reception signal output from the reception unit, in which the information processing unit generates Doppler waveform data based on the reception signal, obtains a maximum value, a minimum value, and a reference value of a Doppler waveform line obtained from the Doppler waveform data, and decides a display range of blood flow velocity indicated by a Doppler waveform based on the maximum value, the minimum value, the reference value.

In one embodiment, the reference value is a Doppler waveform average value, 0, or a centroid of the Doppler waveform.

In one embodiment, the information processing unit decides the display range by multiplying a larger value of an absolute value of a value obtained by subtracting the reference value from the maximum value and an absolute value of a value obtained by subtracting the reference value from the minimum value by a predetermined scale factor.

In one embodiment, the scale factor is decided according to an index value obtained by dividing an absolute value of a value obtained by subtracting the minimum value from the maximum value by a larger value of an absolute value of the maximum value and an absolute value of the minimum value.

In one embodiment, the information processing unit calculates the scale factor according to values of a scale function for obtaining the scale factor using an index value, the scale factor indicating a curve passing through a plurality of set points or a curve approximated to the curve passing through the plurality of set points, the index value is a value indicating a difference between the maximum value and the minimum value, and the set point is a point on a coordinate plane in which the index value and the scale factor are associated with each other.

In one embodiment, the information processing unit sets the set point via a user interface.

In one embodiment, the information processing unit decides the scale factor according to a diagnosis status.

In one embodiment, the information processing unit acquires the scale factor via a user interface.

In one embodiment, the information processing unit acquires a signal indicating pulsation of the subject from a pulsation detection device that detects the pulsation of the subject, and decides the display range at a timing corresponding to the pulsation of the subject.

In one embodiment, a repetition frequency when the transmission unit transmits the ultrasonic wave is set according to the display range.

In one embodiment, the information processing unit decides the display range according to an area of a region between the Doppler waveform line and a reference line indicated by the reference value.

According to the present disclosure, it is possible to set a display state so that a Doppler waveform is easily visible, for an ultrasound diagnostic apparatus.

BRIEF DESCRIPTION OF THE DRAWINGS

FIG. 1 is a diagram showing a configuration of an ultrasound diagnostic apparatus.

DESCRIPTION OF THE PREFERRED EMBODIMENTS

Figure 1:
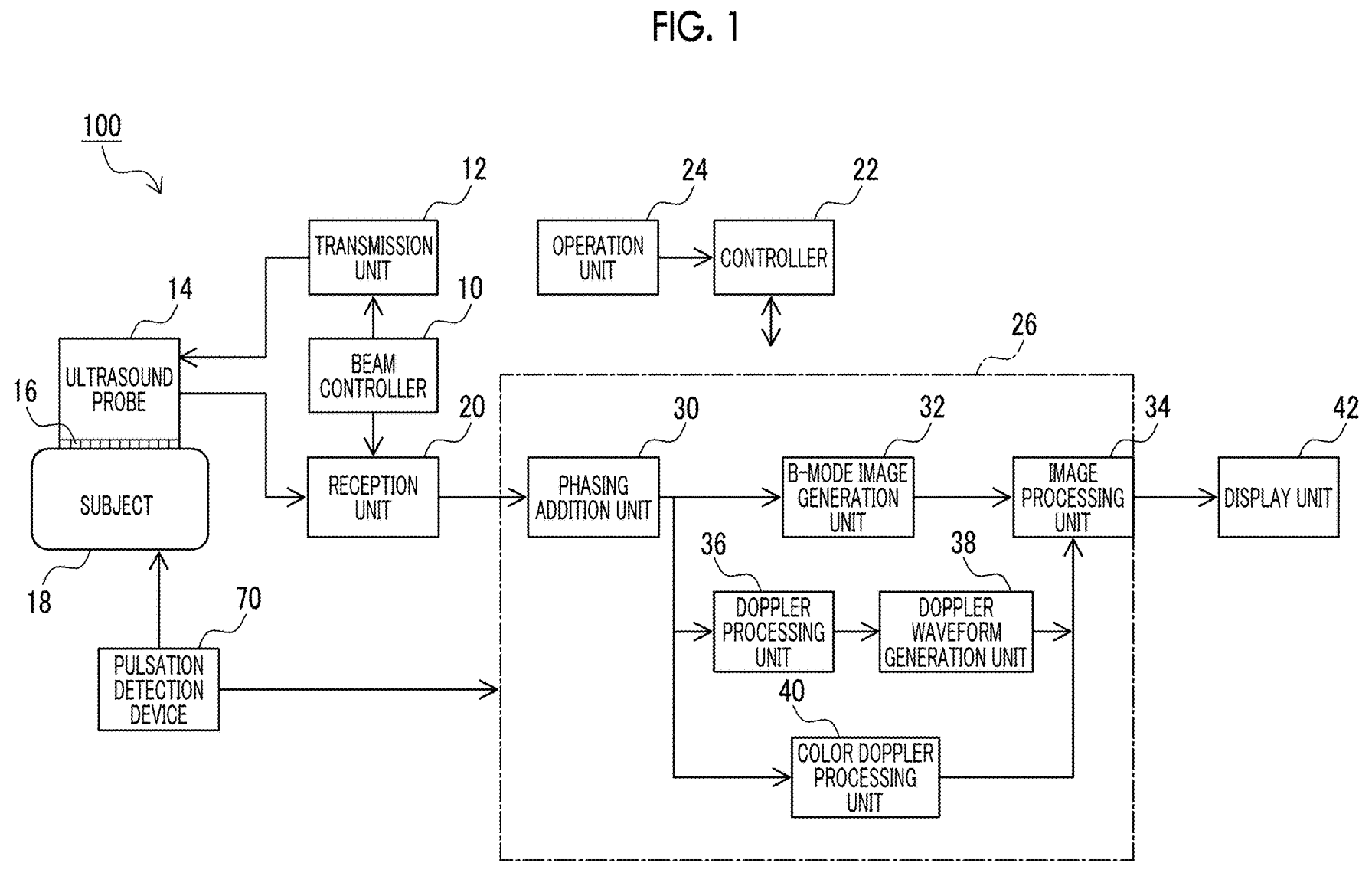
Figure 2:
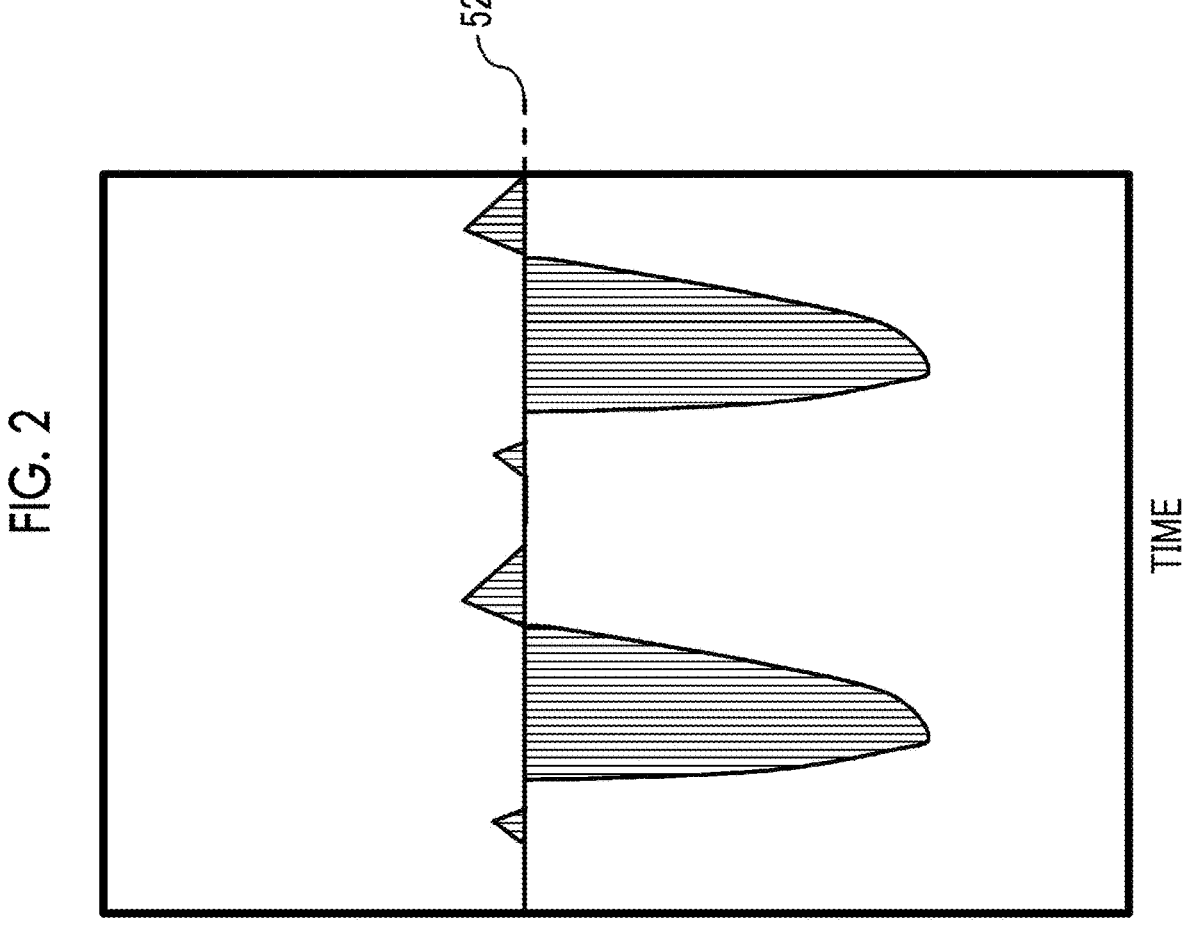
FIG. 2 is a diagram showing an example of a Doppler waveform.

Each embodiment of the present disclosure will be described with reference to each drawing. The same components shown in a plurality of drawings are denoted by the same reference numerals, and the description thereof will not be repeated. FIG. 1 shows a configuration of an ultrasound diagnostic apparatus 100 according to an embodiment of the present disclosure. The ultrasound diagnostic apparatus 100 comprises a beam controller 10, a transmission unit 12, an ultrasound probe 14, a reception unit 20, a controller 22, an operation unit 24, an information processing unit 26, and a display unit 42.

The information processing unit 26 may be configured by one or a plurality of processors that execute a program to realize functions of a phasing addition unit 30, a B-mode image generation unit 32, an image processing unit 34, a Doppler processing unit 36, a Doppler waveform generation unit 38, and a color Doppler processing unit 40. The controller 22 performs overall control of the ultrasound diagnostic apparatus 100. The operation unit 24 includes a keyboard, a mouse, a lever, a button, a voice recognition device, and the like, and outputs information regarding a user's operation to the controller 22. The controller 22 controls the ultrasound diagnostic apparatus 100 in response to an operation on the operation unit 24.

The operation unit 24 may constitute a user interface for operating the ultrasound diagnostic apparatus 100 together with the display unit 42. For example, the operation unit 24 may include a touch panel on a display screen of the display unit 42. In addition, the operation unit 24 may have a function of operating a keyboard, a lever, a button, or the like that is virtually configured on the display screen. The controller 22 may output the information acquired via the user interface to the information processing unit 26.

An outline of an operation of the ultrasound diagnostic apparatus 100 will be described. The ultrasound diagnostic apparatus 100 transmits ultrasonic waves from the ultrasound probe 14 to a subject 18 and receives the ultrasonic waves reflected by the subject 18 via the ultrasound probe 14. The ultrasound diagnostic apparatus 100 executes measurements in B-mode, Doppler mode, and color Doppler mode.

In the B-mode operation, the ultrasound diagnostic apparatus 100 generates B-mode image data based on the ultrasonic waves received from the subject 18, and displays a B-mode image on the display unit 42. In the Doppler mode operation, the ultrasound diagnostic apparatus 100 generates Doppler waveform data regarding blood flow based on a Doppler shift frequency of the ultrasonic waves received from the subject 18, and displays the Doppler waveform on the display unit 42. In the color Doppler mode operation, the ultrasound diagnostic apparatus 100 generates image data showing an image in which a color corresponding to the blood flow velocity is applied to a B-mode image, and displays an image based on the image data on the display unit 42. Only one of the B-mode operation, the Doppler mode operation, or the color Doppler mode operation may be executed, or measurements in two or three of the three modes may be performed in a time division manner.

A specific configuration of the ultrasound diagnostic apparatus 100 and specific processing executed by the ultrasound diagnostic apparatus 100 will be described. The ultrasound probe 14 is in a state of being in contact with a surface of the subject 18. The ultrasound probe 14 comprises a plurality of transducer elements 16. The transmission unit 12 outputs a transmission signal to each of the transducer elements 16 of the ultrasound probe 14 under the control of the beam controller 10. As a result, the ultrasonic waves are transmitted from the ultrasound probe 14. The beam controller 10 controls the transmission unit 12 to form a transmission beam in the ultrasound probe 14 and scan the subject 18 with the transmission beam. That is, the transmission unit 12 adjusts a delay time or a level of each transmission signal in accordance with the control of the beam controller 10, forms a transmission beam in the ultrasound probe 14, and scans the subject 18 with the transmission beam.

In a case in which the ultrasonic waves reflected in the subject 18 are received by each transducer element 16 of the ultrasound probe 14, each transducer element 16 outputs an electric signal corresponding to the received ultrasonic waves to the reception unit 20. The reception unit 20 performs processing, such as amplification, detection, and frequency band limitation, on the reception signal output from each transducer element 16 in accordance with the control of the beam controller 10, and outputs the processed reception signal to the information processing unit 26. The information processing unit 26 performs processing on each reception signal, which is executed by each of the components (the phasing addition unit 30, the B-mode image generation unit 32, the image processing unit 34, the Doppler processing unit 36, the Doppler waveform generation unit 38, and the color Doppler processing unit 40).

The phasing addition unit 30 performs phasing addition of a plurality of the reception signals output from the reception unit 20 for the plurality of transducer elements 16 to generate a phase-adjusted reception signal. As a result, a phase-adjusted reception signal is generated through phase adjustment and addition such that the reception signals based on the ultrasonic waves received in a specific direction strengthen each other, and a reception beam is formed in the specific direction. The phase addition unit 30 outputs the phase-adjusted reception signal to the B-mode image generation unit 32 during the B-mode operation. In addition, the phase addition unit 30 outputs the phase-adjusted reception signal to the Doppler processing unit 36 during the Doppler mode operation and outputs the phase-adjusted reception signal to the color Doppler processing unit 40 during the color Doppler mode operation.

The B-mode operation will be described. The phasing addition unit 30 generates each phase-adjusted reception signal based on the ultrasonic wave received in each direction of the reception beam scanned in the subject 18, and outputs the phase-adjusted reception signal to the B-mode image generation unit 32. The B-mode image generation unit 32 generates B-mode image data based on the phase-adjusted reception signal obtained in each reception beam direction, and outputs the B-mode image data to the image processing unit 34. The B-mode image data based on one scan of the transmission beam and the reception beam (hereinafter, referred to as transmission and reception beams) is image data for one frame and corresponds to one B-mode image.

The beam controller 10, the transmission unit 12, the ultrasound probe 14, the reception unit 20, the phasing addition unit 30, and the B-mode image generation unit 32 generate the B-mode image data one after another in association with repetitive scan of the transmission and reception beams, and output each B-mode image data to the image processing unit 34. The image processing unit 34 generates a video signal for displaying the B-mode image based on the B-mode image data, and outputs the video signal to the display unit 42. The display unit 42 displays the B-mode image based on the video signal.

The Doppler mode operation will be described. The Doppler mode includes a pulse wave Doppler mode (PW Doppler mode) in which an ultrasonic pulse is transmitted at a repetition frequency PRF and a continuous wave Doppler mode (CW Doppler mode) in which the ultrasonic wave is continuously transmitted. Whether to operate in the PW Doppler mode or in the CW Doppler mode may be selected by an operation of the user.

The Doppler processing unit 36 sequentially performs fast Fourier transform processing on the phase-adjusted reception signal divided for a predetermined time length, sequentially generates frequency spectrum data of the Doppler shift frequency with an elapse of time, and outputs the frequency spectrum data to the Doppler waveform generation unit 38. Here, the Doppler shift frequency refers to a frequency representing a shift in frequency of the reception signal with respect to a frequency of the transmission signal.

The Doppler waveform generation unit 38 generates Doppler waveform image data based on a plurality of sets of frequency spectrum data that are sequentially output with the elapse of time. FIG. 2 shows an example of the Doppler waveform indicated by the Doppler waveform data. In the Doppler waveform, a horizontal axis represents time and a vertical axis represents the Doppler shift frequency. The Doppler shift frequency shown on the vertical axis indicates blood flow velocity. Brightness of a plurality of images arranged in the vertical direction at a certain time point on the time axis indicates a frequency spectrum corresponding to the certain time point. A baseline 52 extending linearly in the horizontal direction indicates that the Doppler shift frequency, that is, the blood flow velocity is 0.

The Doppler waveform generation unit 38 sequentially updates the Doppler waveform data with the elapse of time. That is, the Doppler waveform generation unit 38 deletes the frequency spectrum data first obtained from the Doppler waveform data composed of a series of frequency spectrum data, and adds the latest frequency spectrum data to the Doppler waveform data to update the Doppler waveform data. The image processing unit 34 generates a video signal for displaying the Doppler waveform based on the Doppler waveform data and outputs the video signal to the display unit 42. The display unit 42 displays the Doppler waveform based on the video signal.

The color Doppler mode operation will be described. In a case in which the color Doppler processing unit 40 generates the color Doppler data, the ultrasonic waves are transmitted and received a plurality of j times in each direction of the transmission and reception beams. The color Doppler processing unit 40 generates the color Doppler data based on the phase-adjusted reception signals acquired j times in each direction of the transmission and reception beams. The color Doppler data indicates blood flow velocity using color on a B-mode image of a region where scanning with the transmission and reception beams is performed. The color Doppler data may be data in which, for example, a blue color is applied to a region where the blood flows in a direction away from the ultrasound probe 14, a red color is applied to a region where the blood flows in a direction approaching the ultrasound probe 14, and brightness is increased in regions where the blood flow velocity is greater.

The color Doppler processing unit 40 obtains blood flow velocity $v(r)$ in a depth direction of the transmission and reception beams based on the j phase-adjusted reception signals, for example, according to autocorrelation processing shown in JP2016-87302A. Here, $v(r)$ indicates blood flow velocity at a position of depth r. The color Doppler processing unit 40 generates the color Doppler data based on the blood flow velocity $v(r)$ in the depth direction at each depth r obtained in each direction of the transmission and reception beams, and outputs the color Doppler data to the image processing unit 34.

The image processing unit 34 generates data indicating a B-mode color Doppler image in which a color corresponding to the blood flow velocity is applied to the B-mode image, based on the B-mode image data and the color Doppler data. The image processing unit 34 generates a video signal for displaying the B-mode color Doppler image based on the B-mode color Doppler image data, and outputs the video signal to the display unit 42. The display unit 42 displays the B-mode color Doppler image based on the video signal.

The image processing unit 34 may display the B-mode image and the Doppler waveform side by side on the display unit 42. In addition, the image processing unit 34 may display the B-mode color Doppler image and the Doppler waveform side by side on the display unit 42.

Figure 3:
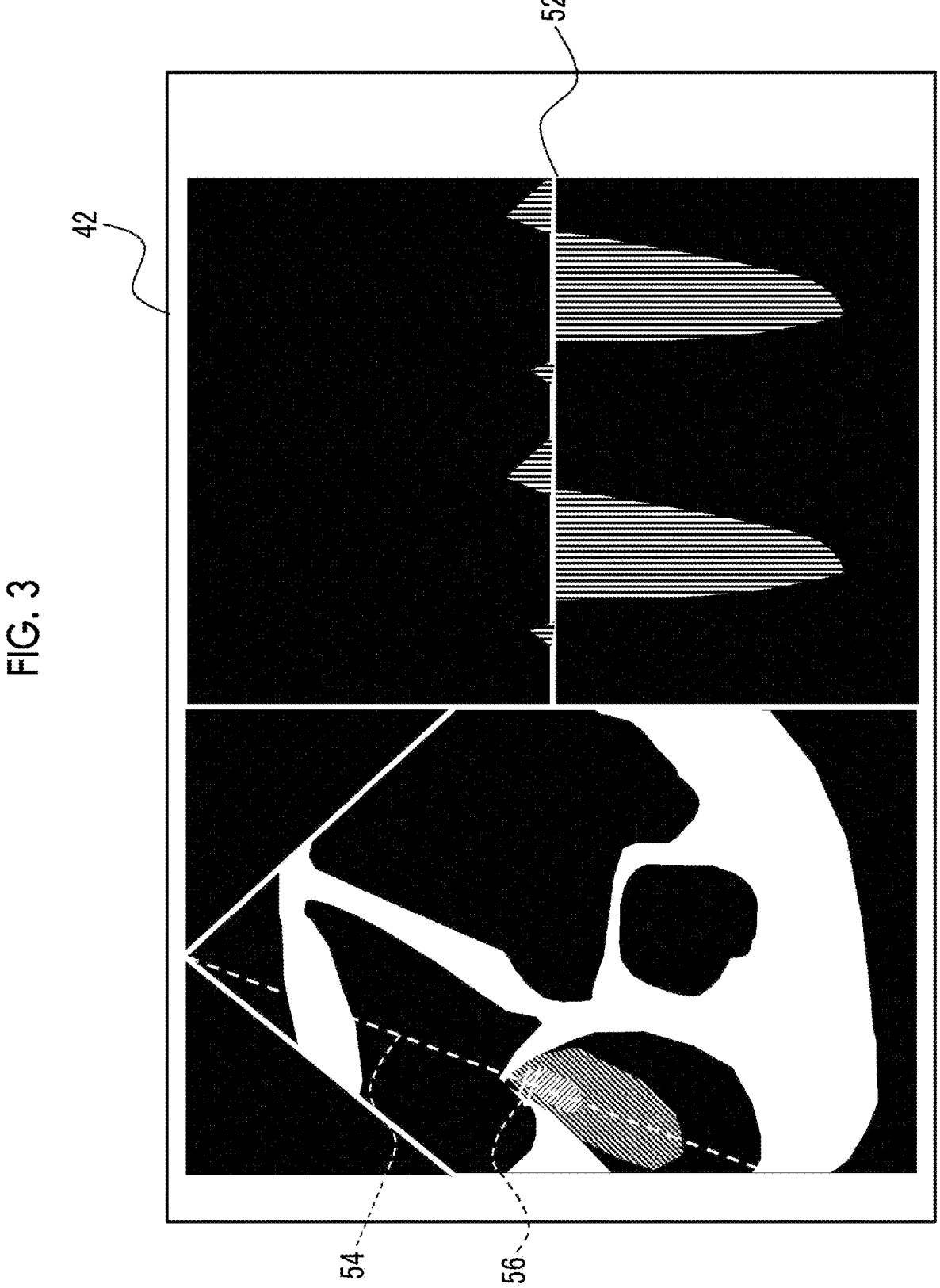
FIG. 3 is a diagram showing an example of a B-mode color Doppler image and a Doppler waveform.

FIG. 3 shows an example of the B-mode color Doppler image and the Doppler waveform displayed on the display unit 42. The B-mode color Doppler image is shown on a left side, and the Doppler waveform is shown on a right side. Each image is acquired in the vicinity of a mitral valve of the heart. The shaded regions in the B-mode color Doppler image are colored regions.

On the B-mode color Doppler image, a beam straight line 54 indicating the direction of the transmission and reception beams in the Doppler mode and a Doppler gate 56 are shown. Here, the Doppler gate 56 refers to a range in which the blood flow velocity on the transmission and reception beams is measured and is set in an image of blood vessels appearing in the B-mode image. A region sandwiched between two parallel straight lines intersecting the beam straight line 54 is the Doppler gate 56, and the blood flow velocity is measured in this range. The controller 22 sets the beam straight line 54 and the Doppler gate 56 in response to the user's operation on the operation unit 24.

In a case in which the image processing unit 34 displays the Doppler waveform, the image processing unit 34 executes scaling. The scaling is a process of deciding a ratio of a swing width of the Doppler waveform to the display range of the display image in the vertical axis direction.

Figure 4:
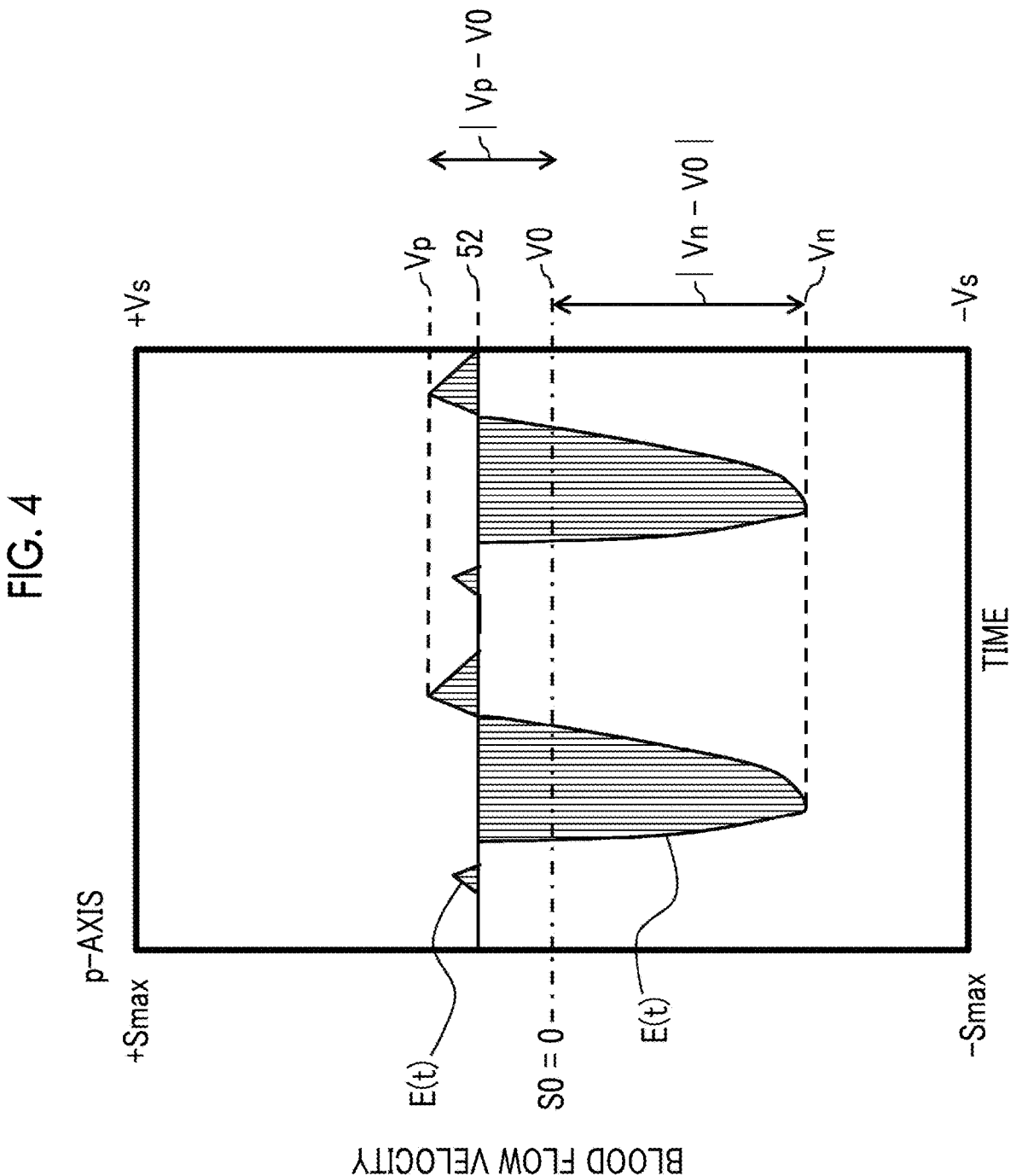
FIG. 4 is a diagram showing a Doppler waveform line together with a Doppler waveform.

FIG. 4 shows a Doppler waveform for describing the scaling. A p-axis is defined as a vertical axis of an image coordinate system in the vertical direction of the display image. A coordinate value of the p-axis indicates a position in the vertical direction in the display image. In addition, a horizontal axis represents time. The image processing unit 34 obtains a display width Vs for each of the positive and negative sides based on the value indicated by the Doppler waveform, as described below. Further, the image processing unit 34 associates a positive value Vs of the display width of the Doppler waveform with an upper limit value of the p-axis in the image coordinate system, and associates a negative value −Vs of the display width of the Doppler waveform with a lower limit value of the p-axis. As a result, the display range of the Doppler waveform is decided to be −Vs or more and Vs or less.

The scaling executed by the image processing unit 34 will be specifically described. The image processing unit 34 obtains a Doppler waveform line E(t) based on the Doppler waveform data. The Doppler waveform line E(t) may be an envelope of the Doppler waveform. That is, the Doppler waveform line E(t) may be defined as a curve on a negative side of the Doppler waveform line E(t) in a positive region above the baseline 52, where a component value of the frequency spectrum corresponding to each time is equal to or greater than a predetermined threshold value. In addition, the Doppler waveform line E(t) may be defined as a curve on a positive side of the Doppler waveform line E(t) in a negative region below the baseline 52, where a component value of the frequency spectrum corresponding to each time is equal to or greater than a predetermined threshold value. FIG. 4 shows the Doppler waveform line E(t) together with the Doppler waveform.

The image processing unit 34 obtains, for example, a Doppler waveform average value in a time range traced back from the current point in time by predetermined N cardiac cycles, where N is a positive integer. The cardiac cycle may be measured by a pulsation signal output from a pulsation detection device 70 that detects the pulsation of the subject 18. The pulsation detection device 70 may be, for example, an electrocardiogram device. The pulsating signal may be a signal indicating an electrocardiogram. The Doppler waveform average value may be defined as a value obtained by averaging a midpoint value (half the value obtained by adding an upper limit value and a lower limit value) of the blood flow velocity range, where the component value of the frequency spectrum is equal to or greater than a predetermined threshold value, in a time range traced back from the current point in time by predetermined N cardiac cycles. The image processing unit 34 sets the Doppler waveform average value as a reference value V0. In addition, the image processing unit 34 obtains a maximum value Vp and a minimum value Vn of the Doppler waveform line E(t) in the time range traced back from the current point in time by the N cardiac cycles. The image processing unit 34 may obtain a maximum value Vp, a minimum value Vn, and a Doppler waveform average value in a time range traced back from the current point in time by a predetermined time.

The image processing unit 34 obtains a larger value of an absolute value |Vp−V0| of a value obtained by subtracting the reference value V0 from the maximum value Vp, and an absolute value |Vn−V0| of a value obtained by subtracting the reference value V0 from the minimum value Vn, as the swing width SW. That is, the image processing unit 34 obtains the swing width SW according to SW=max(|Vp−V0|,|Vn−V0|). Here, "max" indicates the maximum value of the values listed in the parentheses following "max".

The image processing unit 34 multiplies a predetermined scale factor k by the swing width SW to obtain the display width Vs as Vs=k·SW. The image processing unit 34 associates a positive value +Vs of the display width with an upper limit value Smax of the display range of the p-axis in the image coordinate system, and associates a negative value −Vs of the display width with a lower limit value −Smax of the display range of the p-axis in the image coordinate system. In addition, the image processing unit 34 associates the reference value V0 with a central value S0 of the display range of the p-axis.

The image processing unit 34 converts the value indicated by the Doppler waveform into the coordinate value of the p-axis such that an upper end of the display image indicates +Vs, a lower end of the display image indicates −Vs, and a central position of the display range in the vertical direction indicates the reference value V0. The image processing unit 34 generates a video signal for displaying the Doppler waveform based on the Doppler waveform data in which the value indicated by the Doppler waveform is converted into the coordinate value of the p-axis, and outputs the video signal to the display unit 42. The display unit 42 displays an image showing the Doppler waveform based on the video signal.

The scale factor k may be decided in advance based on a diagnosis result or the like performed in the past. The scale factor k may be read via the user interface. That is, the image processing unit 34 may acquire the scale factor k via the user interface and the controller 22. In a case of observing the vicinity of the mitral valve, the scale factor k may be, for example, 1.1 or more and less than 1.8.

In the example shown in FIG. 4, the swing width $$SW = \max(|Vp - V0|, |Vn - V0|)$$

is $$SW = |Vn - V0|, -Vs = -|Vn - V0|$$

is associated with the lower limit value of the p-axis, and $$+Vs = |Vn - V0|$$

is associated with the upper limit value of the p-axis.

The scale factor k may be decided based on an n-th degree polynomial as a scale function as shown in (Expression 1).

$$k = \alpha(n)x^n + \alpha(n-1)x^{n-1} + \ldots + \alpha(1)x + \alpha(0) \qquad \text{Expression 1}$$

Note that the index value x is a value indicating a difference between the maximum value Vp and the minimum value Vn, and is defined by (Expression 2).

$$x = |Vp - Vn|/\max(|Vp|, |Vn|) \qquad \text{Expression 2}$$

The n+1 coefficients α(0) to α(n) are obtained as follows. First, the user sets n+1 set points on an xk coordinate plane in which a vertical axis is k and a horizontal axis is x. Then, the coefficients α(0) to α(n) are obtained such that a curve indicated by the scale function passes through the n+1 set points or is approximated to the curve that passes through the n+1 set points. The coefficients α(0) to α(n) may be obtained according to a least squares method, a spline interpolation method, or the like. The user may set the set point via the user interface constituted by the operation unit 24 and the display unit 42.

Figure 5:
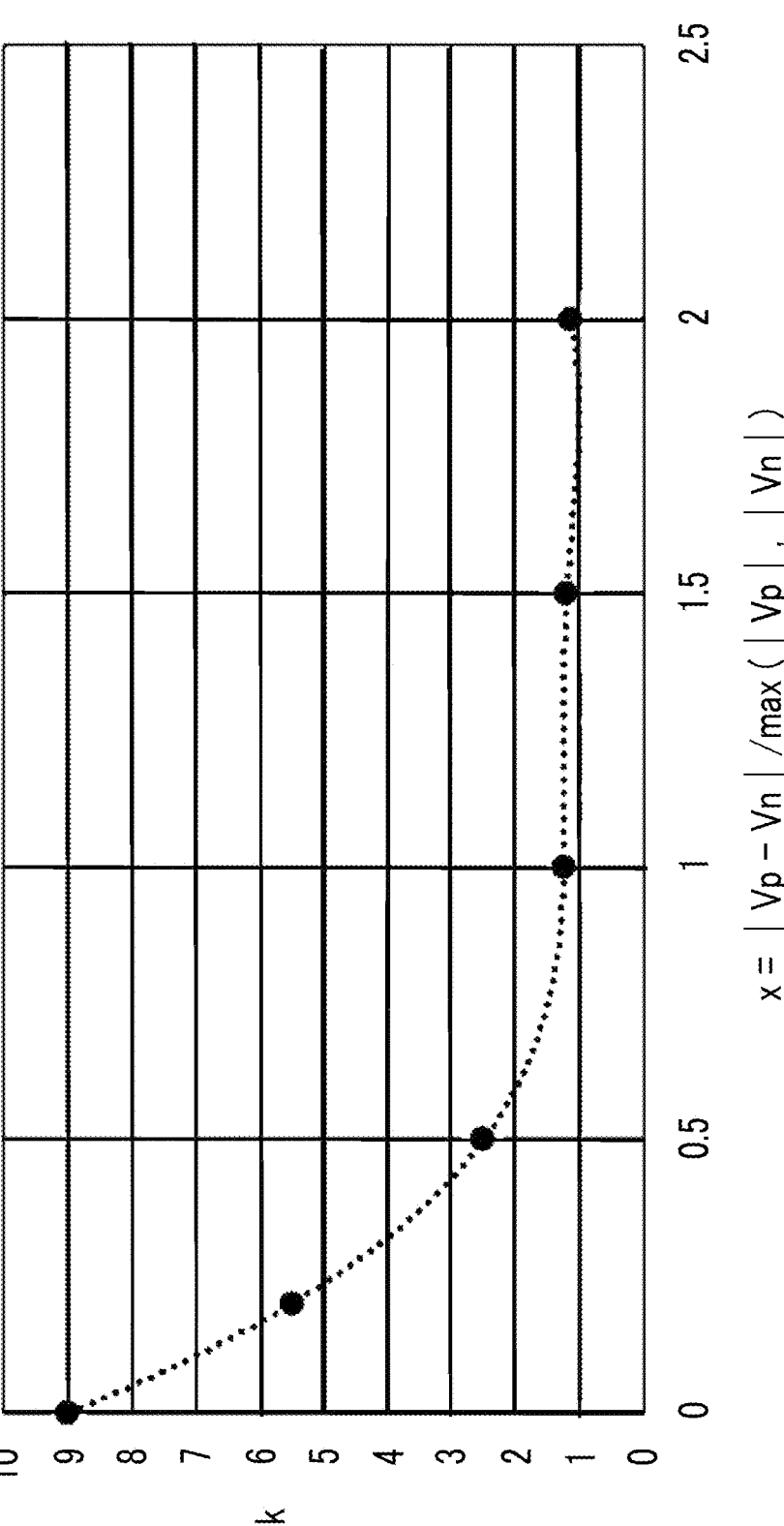
FIG. 5 is a diagram showing an example of a scale function.

FIG. 5 shows an example of the scale function. This scale function is obtained by designating six set points on the xk coordinate plane by the user and obtaining each coefficient of a quintic polynomial for complementing the six set points.

Specifically, the scale function shown in FIG. 5 is represented as (Expression 3) with n=5, $\alpha(0)$=9, $\alpha(1)$=−20.936, $\alpha(2)$=17.829, $\alpha(3)$=−2.7052, $\alpha(4)$=−2.897, and $\alpha(5)$ =0.9594.

$$k = 0.9594x^5 - 2.897x^4 - 2.7052x^3 + 17.829x^2 - 20.936x + 9 \quad \text{Expression 3}$$

Waveform characteristic values such as a maximum value, a minimum value, and a Doppler waveform average value of the Doppler waveform vary depending on an observation site. Therefore, in a case in which the Doppler waveform is displayed at a certain scale, it may become difficult to see the Doppler waveform. According to the process of obtaining the scale factor k based on the scale function, the scale factor k is obtained by giving the index value x based on the maximum value Vp of the Doppler waveform line E(t) and the minimum value Vn of the Doppler waveform line E(t) to the scale function. As a result, an appropriate scale factor k is obtained even though the maximum value Vp of the Doppler waveform line E(t) and the minimum value Vn of the Doppler waveform line E(t) change in accordance with a change in the observation site.

As described above, the information processing unit 26 obtains the index value x by dividing an absolute value of a value obtained by subtracting the minimum value Vn of the Doppler waveform line E(t) from the maximum value Vp of the Doppler waveform line E(t) by a larger value of an absolute value of the maximum value Vp and an absolute value of the minimum value Vn, as shown in (Expression 2). The information processing unit 26 decides the scale factor k by giving the index value x to the scale function shown in (Expression 1).

The information processing unit 26 decides the display range by multiplying a larger value of an absolute value of a value obtained by subtracting the reference value V0 from the maximum value Vp of the Doppler waveform line E(t) and an absolute value of a value obtained by subtracting the reference value V0 from the minimum value Vn of the Doppler waveform line E(t) by the scale factor k. That is, the information processing unit 26 obtains the swing width SW according to $$SW = \max(|Vp - V0|, |Vn - V0|),$$

and decides a range of −k·SW or more and k·SW or less as the display range of the Doppler waveform.

Figure 6:
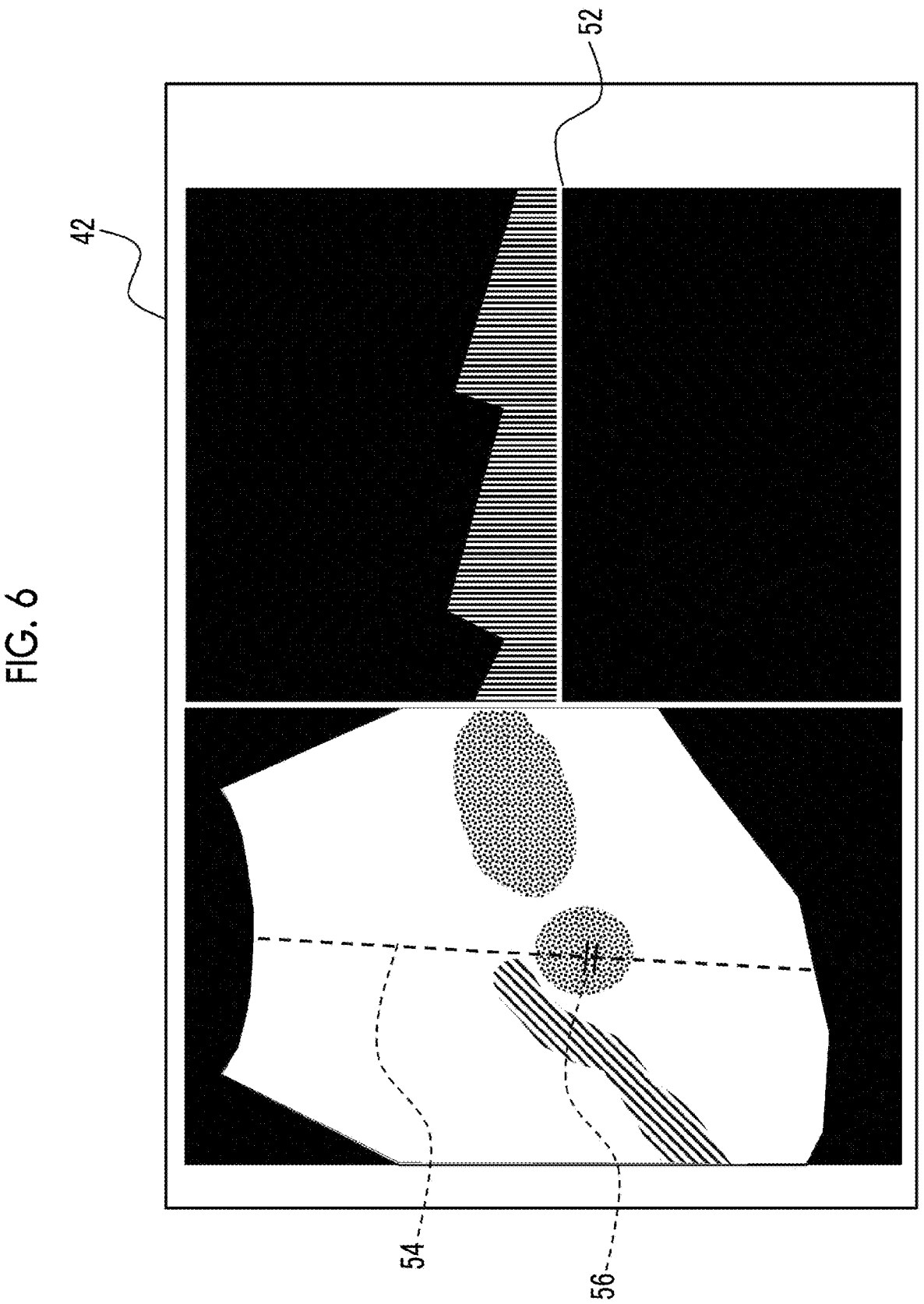
FIG. 6 is a diagram showing an example of a B-mode color Doppler image and a Doppler waveform.
Figure 7:
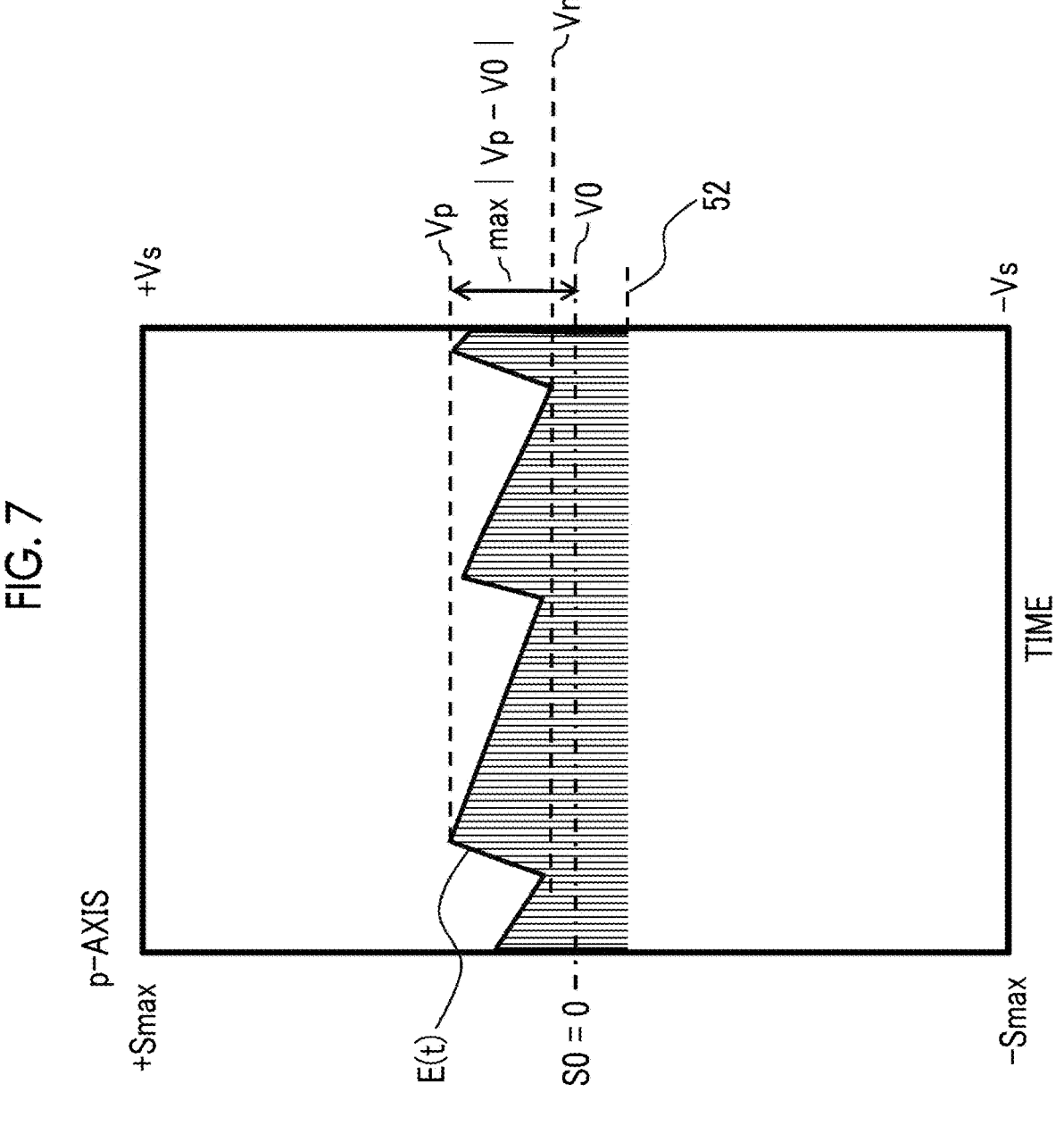
FIG. 7 is a diagram showing a Doppler waveform line together with a Doppler waveform.

An example of a B-mode color Doppler image acquired in the vicinity of the abdominal aorta is shown on a left side of FIG. 6. A Doppler waveform acquired in the vicinity of the abdominal aorta is shown on a right side of FIG. 6. In addition, FIG. 7 shows a Doppler waveform line E(t) together with the Doppler waveform. In the vicinity of the abdominal aorta, unlike the vicinity of the mitral valve of the heart, the direction of blood flow is unidirectional. In the example shown in FIG. 7, the reference value V0 is on a positive side with respect to the baseline 52, and the swing width SW is $$SW = \max(|Vp - V0|, |Vn - V0|) = Vp - V0.$$

The image processing unit 34 multiplies the scale factor k by the swing width SW to obtain the display width Vs as $$Vs = k \cdot SW.$$

In a case of observing the vicinity of the abdominal aorta, the scale factor k may be, for example, 1.8 or more and less than 3.2.

Figure 8:
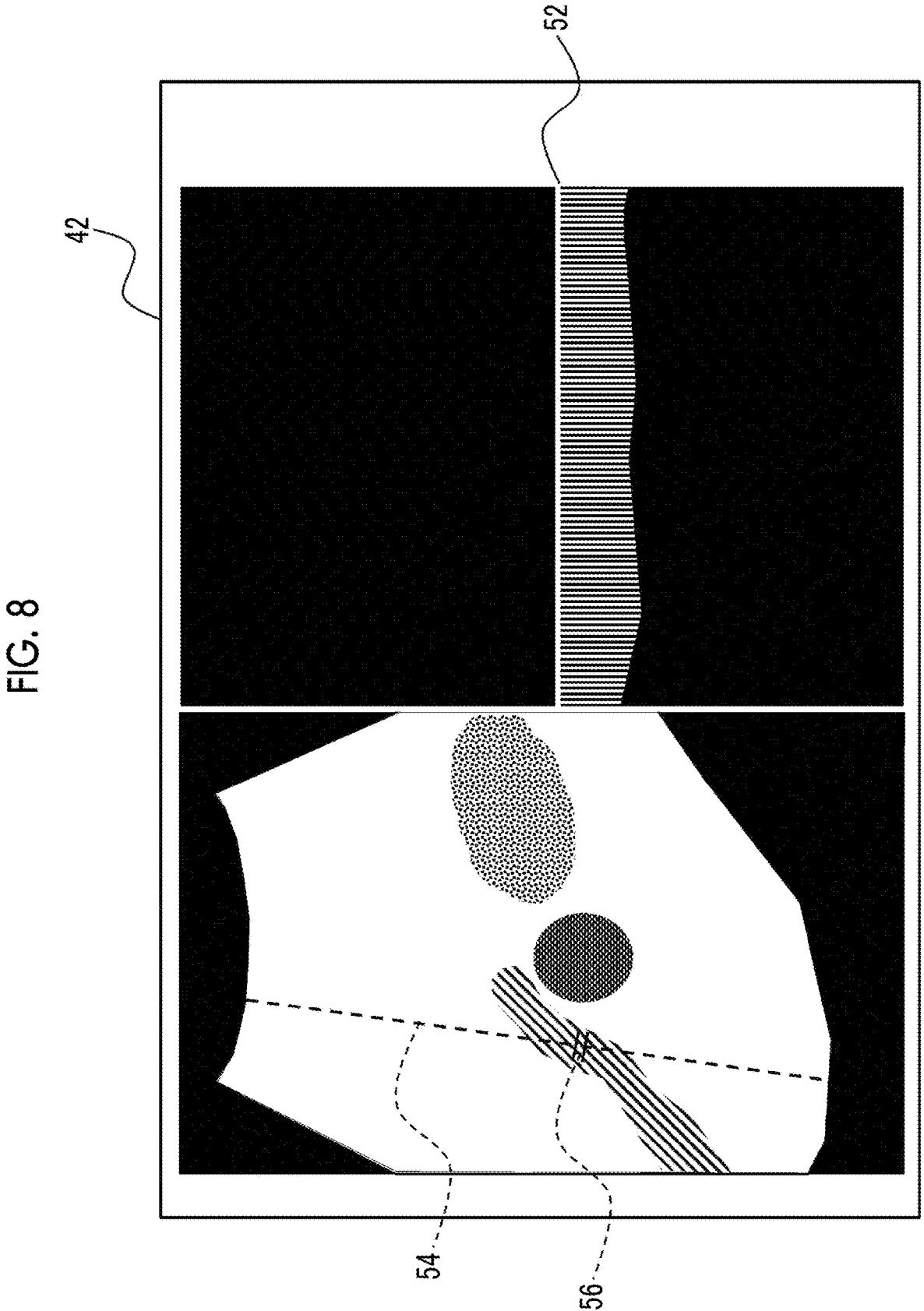
FIG. 8 is a diagram showing an example of a B-mode color Doppler image and a Doppler waveform.
Figure 9:
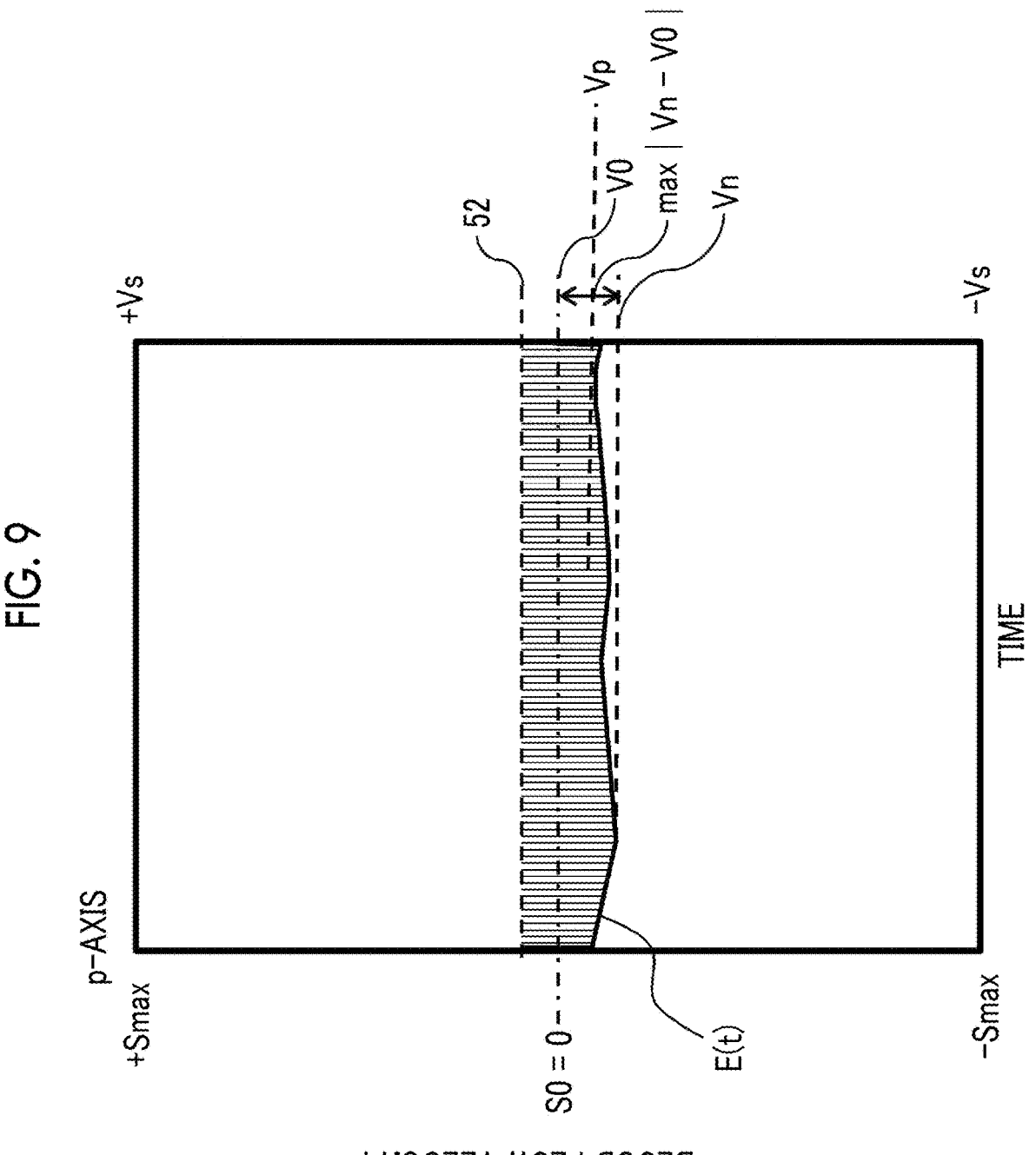
FIG. 9 is a diagram showing a Doppler waveform line together with a Doppler waveform.

An example of a B-mode color Doppler image acquired in the vicinity of the portal vein of the liver is shown on a left side of FIG. 8. A Doppler waveform acquired in the vicinity of the portal vein is shown on aright side of FIG. 8. In addition, FIG. 9 shows a Doppler waveform line E(t) together with the Doppler waveform. In the vicinity of the portal vein, unlike the vicinity of the mitral valve of the heart, the direction of blood flow is unidirectional. In the example shown in FIG. 9, the reference value V0 is on a negative side with respect to the baseline 52, and the swing width SW is $$SW = \max(|Vp - V0|, |Vn - V0|) = V0 - Vn.$$

The image processing unit 34 multiplies the scale factor k by the swing width SW to obtain the display width Vs as $$Vs = k \cdot SW.$$

In a case of observing the vicinity of the portal vein, the scale factor k may be, for example, 2.4 or more and less than 9.0.

The image processing unit 34 may decide the scale factor k based on an area between the Doppler waveform line E(t) and the reference line indicating the reference value V0. The image processing unit 34 obtains a time integral value of $$|Et(t) - V0|,$$

for example, in a time range traced back from the current point in time by predetermined N cardiac cycles or in a time range traced back from the current point in time by a predetermined time. The image processing unit 34 may increase the scale factor k as the time integral value decreases. The image processing unit 34 may decide the scale factor k such that a proportion R occupied by a region sandwiched between k times the Doppler waveform line E(t) and the reference line in the display image is equal to or more than a certain threshold value Th1 and equal to or less than a certain threshold value Th2 (Th1≤R≤Th2).

In the above description, an embodiment is shown in which the reference value V0 is the Doppler waveform average value. The reference value V0 may be 0 or may be the centroid of the Doppler waveform. The centroid of the Doppler waveform is defined, for example, as a value obtained by calculating a weighted average value of the blood flow velocity using the component values of the frequency spectrum as weighting values for each time point, and further averaging these weighted average values of the blood flow velocity in a time range traced back from the current point in time by predetermined N cardiac cycles. In addition, the centroid of the Doppler waveform may be defined as a value obtained by averaging the weighted average values of the blood flow velocity in a time range traced back from the current point in time by a predetermined time.

Figure 10:
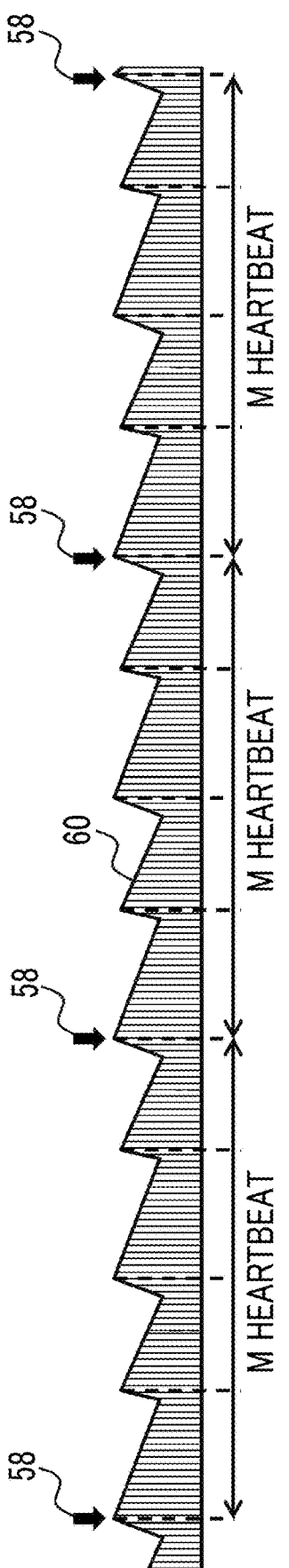
FIG. 10 is a diagram showing an update timing of a scale factor.
Figure 11:
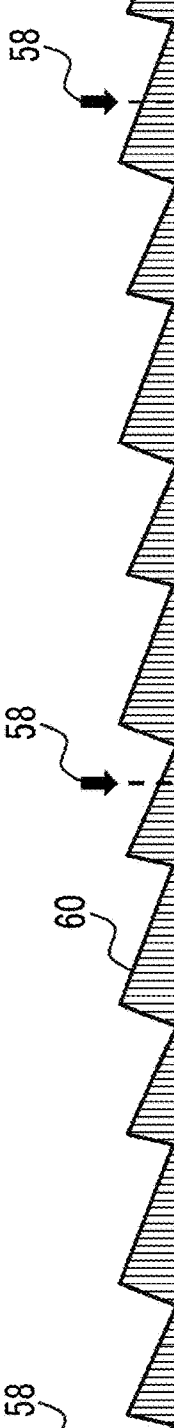
FIG. 11 is a diagram showing an update timing of a scale factor.

The image processing unit 34 may update the scale factor k at a timing corresponding to the pulsation of the subject 18. For example, the image processing unit 34 may update the scale factor k for each M cardiac cycle, where M is a positive integer. FIG. 10 conceptually shows an update timing 58 of the scale factor k and the Doppler waveform 60 in a case in which the scale factor k is updated for each M cardiac cycle. In addition, the image processing unit 34 may update the scale factor k for each update cycle T, where T is an update cycle. FIG. 11 conceptually shows an update timing 58 of the scale factor k and the Doppler waveform 60 in a case in which the scale factor k is updated for each update cycle T.

In addition, in a case in which an operation for updating the scale factor k is performed by the operation unit 24, the image processing unit 34 may update the scale factor k.

The image processing unit 34 may automatically set the scale factor k according to a diagnosis status. The diagnosis status is specified by, for example, an observation site such as the heart, liver, or abdomen, and a lesion that may be found in each observation site. The image processing unit 34 may recognize the diagnosis status via the user interface.

In a case in which the Doppler mode is the PW Doppler mode, the controller 22 may adjust the repetition frequency PRF such that the aliasing phenomenon does not occur on the display image. Here, the aliasing phenomenon refers to phenomenon in which the Doppler waveform is periodically repeated and displayed in the vertical axis direction. In a case in which the scale factor k is increased, the controller 22 may control the beam controller 10, the transmission unit 12, the reception unit 20, and the information processing unit 26 such that the repetition frequency PRF is increased to a level at which the aliasing phenomenon is avoided. In addition, in a case in which the scale factor k is reduced, the controller 22 may control the beam controller 10, the transmission unit 12, the reception unit 20, and the information processing unit 26 such that the repetition frequency PRF is reduced. By reducing the repetition frequency PRF, a display resolution in the vertical axis direction is improved.

Configuration of Present Disclosure

Configuration 1:
An ultrasound diagnostic apparatus comprising:
a transmission unit that transmits an ultrasonic wave to a subject via an ultrasound probe;
a reception unit that receives the ultrasonic wave reflected by the subject via the ultrasound probe; and
an information processing unit that executes processing on a reception signal output from the reception unit,
in which the information processing unit
generates Doppler waveform data based on the reception signal,
obtains a maximum value, a minimum value, and a reference value of a Doppler waveform line obtained from the Doppler waveform data, and
decides a display range of blood flow velocity indicated by a Doppler waveform based on the maximum value, the minimum value, the reference value.

Configuration 2:
The ultrasound diagnostic apparatus according to Configuration 1,
in which the reference value is a Doppler waveform average value, 0, or a centroid of the Doppler waveform.
Configuration 3:
The ultrasound diagnostic apparatus according to Configuration 1 or 2,
in which the information processing unit decides the display range by multiplying a larger value of an absolute value of a value obtained by subtracting the reference value from the maximum value and an absolute value of a value obtained by subtracting the reference value from the minimum value by a predetermined scale factor.
Configuration 4:
The ultrasound diagnostic apparatus according to Configuration 3,
in which the scale factor is decided according to an index value obtained by dividing an absolute value of a value obtained by subtracting the minimum value from the maximum value by a larger value of an absolute value of the maximum value and an absolute value of the minimum value.
Configuration 5:
The ultrasound diagnostic apparatus according to Configuration 3,
in which the information processing unit calculates the scale factor according to values of a scale function for obtaining the scale factor using an index value, the scale factor indicating a curve passing through a plurality of set points or a curve approximated to the curve passing through the plurality of set points,
the index value is a value indicating a difference between the maximum value and the minimum value, and
the set point is a point on a coordinate plane in which the index value and the scale factor are associated with each other.
Configuration 6:
The ultrasound diagnostic apparatus according to Configuration 5,
in which the information processing unit sets the set point via a user interface.
Configuration 7:
The ultrasound diagnostic apparatus according to Configuration 3,
in which the information processing unit decides the scale factor according to a diagnosis status.
Configuration 8:
The ultrasound diagnostic apparatus according to Configuration 3,
in which the information processing unit acquires the scale factor via a user interface.
Configuration 9:
The ultrasound diagnostic apparatus according to any one of Configuration 1 to Configuration 8,
in which the information processing unit
acquires a signal indicating pulsation of the subject from a pulsation detection device that detects the pulsation of the subject, and
decides the display range at a timing corresponding to the pulsation of the subject.
Configuration 10:
The ultrasound diagnostic apparatus according to any one of Configuration 1 to Configuration 9,
in which a repetition frequency when the transmission unit transmits the ultrasonic wave is set according to the display range.

US 12,678,125 B2

13

Configuration 11:

The ultrasound diagnostic apparatus according to any one of Configuration 1 to Configuration 10, in which the information processing unit decides the display range according to an area of a region between the Doppler waveform line and a reference line indicated by the reference value.

What is claimed is:

1. An ultrasound diagnostic apparatus comprising:

a transmission unit that transmits an ultrasonic wave to a subject via an ultrasound probe;

a reception unit that receives the ultrasonic wave reflected by the subject via the ultrasound probe; and an information processing unit that executes processing on a reception signal output from the reception unit, wherein the information processing unit generates Doppler waveform data based on the reception signal, obtains a maximum value, a minimum value, and a reference value of a Doppler waveform line obtained from the Doppler waveform data, decides a display range of blood flow velocity indicated by a Doppler waveform based on the maximum value, the minimum value, the reference value, and decides the display range by multiplying a larger value of an absolute value of a value obtained by subtracting the reference value from the maximum value and an absolute value of a value obtained by subtracting the reference value from the minimum value by a predetermined scale factor, and wherein the predetermined scale factor is decided according to an index value obtained by dividing an absolute value of a value obtained by subtracting the minimum value from the maximum value by a larger value of an absolute value of the maximum value and an absolute value of the minimum value.

2. An ultrasound diagnostic apparatus comprising:

a transmission unit that transmits an ultrasonic wave to a subject via an ultrasound probe;

a reception unit that receives the ultrasonic wave reflected by the subject via the ultrasound probe; and an information processing unit that executes processing on a reception signal output from the reception unit, wherein the information processing unit generates Doppler waveform data based on the reception signal, obtains a maximum value, a minimum value, and a reference value of a Doppler waveform line obtained from the Doppler waveform data, decides a display range of blood flow velocity indicated by a Doppler waveform based on the maximum value, the minimum value, the reference value, and decides the display range by multiplying a larger value of an absolute value of a value obtained by subtracting the reference value from the maximum value and an absolute value of a value obtained by subtracting the reference value from the minimum value by a predetermined scale factor, wherein the information processing unit calculates the predetermined scale factor according to values of a scale function for obtaining the predetermined scale factor using an index value, the scale function indicating a curve passing through a plurality of set points or a curve approximated to the curve passing through the plurality of set points, the index value is a value indicating a difference between the maximum value and the minimum value, and one of the plurality of set points is a point on a coordinate plane in which the index value and the predetermined scale factor are associated with each other.

3. The ultrasound diagnostic apparatus according to claim 2, wherein the information processing unit sets the set point via a user interface.

*  *  *  *  *